United States Patent [19]
Sueyasu et al.

[11] Patent Number: 5,258,620
[45] Date of Patent: Nov. 2, 1993

[54] METHOD AND APPARATUS FOR DETERMINING THE CONSTITUENTS OF DAIRY PRODUCTS

[75] Inventors: Ryoichi Sueyasu, Yamanashi; Mayumi Watanabe, Chino; Kazuhiko Sagara; Hidehiko Kaya, both of Yamanashi, all of Japan

[73] Assignee: Snow Brand Milk Products Co., Ltd., Hokkaido, Japan

[21] Appl. No.: 773,921

[22] Filed: Oct. 30, 1991

[30] Foreign Application Priority Data

Jun. 15, 1990 [JP] Japan .................. 2-156750

[51] Int. Cl.$^5$ .............................................. G01N 33/04
[52] U.S. Cl. ........................................ 250/339; 250/343
[58] Field of Search ................ 250/339, 340, 341, 343

[56] References Cited

U.S. PATENT DOCUMENTS

| | | | |
|---|---|---|---|
| 3,161,768 | 12/1964 | Goulden | 250/339 |
| 4,236,075 | 11/1980 | Nexo et al. | 250/343 |
| 5,017,785 | 5/1991 | Räsänen | 250/339 X |
| 5,021,662 | 6/1991 | Johnson | 250/339 |

FOREIGN PATENT DOCUMENTS

| | | | |
|---|---|---|---|
| 188750 | 12/1966 | U.S.S.R. | 250/343 |
| 420914 | 8/1974 | U.S.S.R. | 250/341 |
| 1064195 | 12/1983 | U.S.S.R. | 250/341 |

Primary Examiner—Constantine Hannaher
Assistant Examiner—Edward J. Glick
Attorney, Agent, or Firm—Griffin Butler Whisenhunt & Kurtossy

[57] ABSTRACT

A sample having a specific optical path length of 1 to 15 mm is irradiated with near infrared of two or more wavelengths selected from 700 to 1200 nm to determine constituents of dairy products. Preferably, a pair of specific wavelengths comprise a first wavelength having a high correlation with a target constituent and a second wavelength having a low correlation with the target constituent or comprise wavelengths both having high correlations with the target constituent. Quantities of near infrared of these two specific wavelengths transmitted by the sample are measured to determine absorbencies and a multiple linear regression equation is used to calculate the constitutent on the basis of the absorbencies.

7 Claims, 2 Drawing Sheets

METHOD AND APPARATUS FOR DETERMINING THE CONSTITUENTS OF DAIRY PRODUCTS

The present invention relates to method and apparatus for nondestructive, rapid determination of the principal constituents of dairy products such as skim milk, milk, cream and cheese.

BACKGROUND OF THE INVENTION

Analysis of water, fat, protein and salt contents in processed cheese or natural cheese has conventionally been carried out according to the methods prescribed for particular chemical compositions (i.e., official methods of analysis) comprising, for example, the steps of chopping respective samples and treating them with chemicals. However, these methods of the prior art have been inconvenient from various viewpoints. For example, intricate procedures and a relatively long time are usually required to obtain the desired analysis results.

Recently, a method utilizing near infrared analysis for principal constituent analysis has been developed and such method has been employed in the cheese industry to determine values of chemical components other than the salts. However, many of these attempts have used a wavelength range of 1100 to 2500 nm, relying on reflectivity as the means of measurement (Joseph F. Frank J. Dairy Sci. 65.1110-1116, 1982) and with this method there is no means for a determination of the content of salts in cheese.

Such conventional reflectivity measurement utilizes a long wavelength region of the near infrared and has been inevitably accompanied, in the case of milk, with standard deviations of 0.076% for the entire solid components, 0.048% for fat, 0.046% for protein and 0.053% for lactose and, in the case of natural cheese, 1.53% for water, 1.51% for fat and 2.20% for protein. Thus, the precision of analysis has been significantly low in the case of cheese.

In this conventional method, intricate operation of sampling is required, since a specular surface, as smooth as possible, must be provided in order the reflectivity method of measurement may be effectively carried out; and no improvement of such well known method has been achieved to overcome the low precision of analysis of cheese components and to accelerate the operation of the measurement.

For milk, on the other hand, the so-called milkoscan analysis has been practically employed as a relatively speedy method of measurement, but, when this method is employed to determine the fat content in milk, fat globules must be crushed under a uniform pressure of approximately 300 kg/cm$^2$ for homogenization and special equipment is necessary to achieve this.

Furthermore, the ash content of milk can not be determined by using such infrared method and, consequently, the analyzers commonly used in practice have been unable to handle such components except as fixed values.

Moreover, when the near infrared region is used in a range of 1100 to 2500 nm, as commonly been used, for analysis of milk components, the optical path length for the sample has had to be less than 0.5 mm because of the wavelength used and this requirement has often caused sample error. As a consequence, it has been difficult for the subsequent run of an analysis to provide high reproducibility because of the small quantity of sample within that optical path length of a previous run.

In this manner, both the infrared and the near infrared region from 1100 to 2500 nm which have been commonly utilized have encountered the above-mentioned problems. On the other hand, a determination of milk components utilizing the near infrared region having a wavelength from 700 to 1200 nm has not been reported in the art.

The object of the present invention is to determine values of principal components of skim milk, milk, cream and cheese without any pretreatment such as homogenization or treatment with chemicals.

As will be apparent from the foregoing, in the conventional determination utilizing the near infrared region from 1100 to 2500 nm or the infrared region, the method of measurement has been limited to the reflectivity method, and depending on the particular subjects, when a transmittance method of measurement can be employed, the optical path for a sample has had to be set to a length less than 0.5 mm. Therefore, it has usually been difficult to achieve a sample path length sufficient to obtain high reproducibility. In addition, dairy products cover a variety of items such as milk and skim milk in liquid state, on one hand, and butter, cheese etc. in solid state, on the other hand. Particularly for solid state items, the optical path for the sample must be prolonged and, to this end, the wavelength of near infrared must be correspondingly shortened. However, the near infrared region from 1800 to 2500 nm spans a range corresponding to the first absorption band which is most sharp in the NIR region and includes a strong absorption band substantially over the entire range while the near infrared region from 600 to 1100 nm corresponds to the second overtone bands in which the absorption is too weak to obtain adequate information. Accordingly, the reflectivity method of measurement has not been employed in the latter region.

In view of these problems, the inventors have devoted themselves to improvements and developed a novel method utilizing the near infrared having a wavelength from 700 to 1200 nm to determine a quantity of radiation transmitted by a sample and then using results of this determination to make a calibration curve by multiple linear regression so that the above-mentioned drawback of the second overtone bands may be adequately compensated and even the solid dairy products such as cheese can be nondestructively analyzed.

SUMMARY OF THE INVENTION

With the method according to the present invention, two or more specific near infrared bands having wavelengths of 700 to 1200 nm and a specific optical path length of 1 to 15 mm are used. The quantities of the near infrared having said specific wavelengths that are transmitted by a sample are measured to determine respective absorbancies and, based on said absorbancies, an equation of multiple linear regression is employed to calculate the desired component values.

This method allows the principal components of the dairy products such as milk, natural cheese and processed cheese to be rapidly and nondestructively determined without any pretreatment such as homogenization or treatment with chemicals. More specifically, six components of milk or four components of cheese can be simultaneously analyzed in approximately in 30 sec. for every subject.

The method of the invention further can determine the ash content of conventional milk components, while a conventional analyzer utilizing the infrared region has not been able to do so.

The method of this invention as has been described above can be executed by using a dairy product component analyzer utilizing near infrared comprising photoelectric converter means to receive near infrared propagated by a Michelson interferometric optical system, then by a spectroscopic filter and transmitted by a sample contained in a cell and to output absorbancies in the form of photoelectric conversion signals. Also, means to amplify the absorbancies thus outputted are provided, as well means for digital conversion of the amplified absorbancies and means to process the digitally converted electric signals, wherein the spectroscopic filter has two or more specific wavelengths selected from short wave ranges from 700 to 800 nm, 820 to 950 nm, 960 to 1060 nm and 1070 to 1200 nm and the sample cell has an optical path length selected from a range from 1 to 15 mm, preferably 2 to 10 mm.

DESCRIPTION OF PREFERRED EMBODIMENTS

Figure 1:
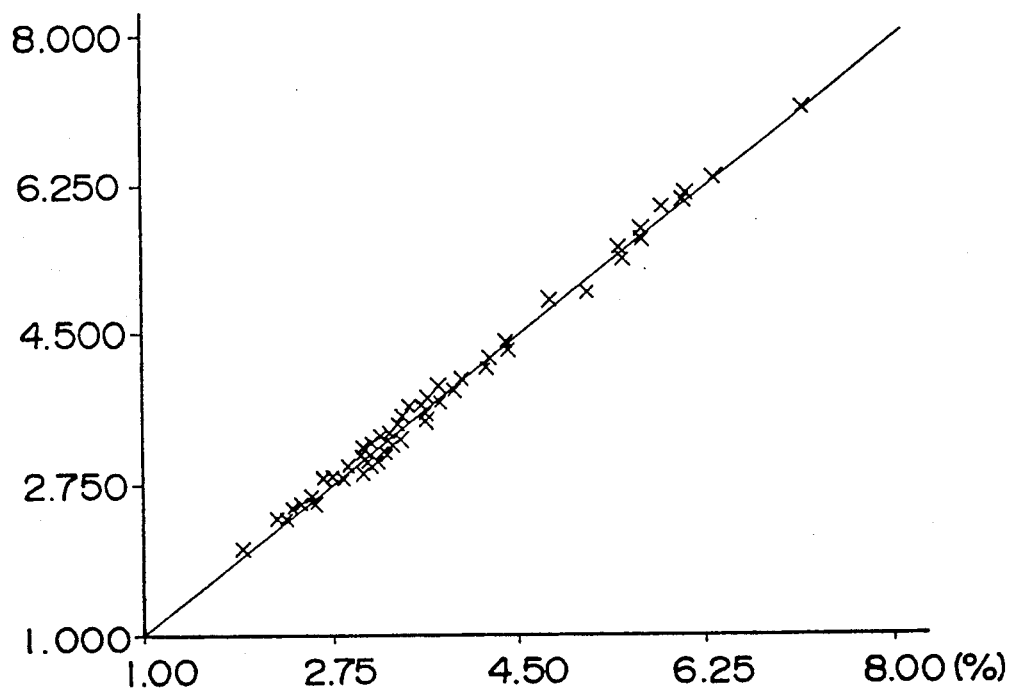
FIG. 1 is a graphic diagram illustrating a correlation between the analytic values of fat contents in 75 milk samples obtained by the official method of measurement and the analytic values thereof obtained by the method of the present invention.

In the first place, the method of the invention will be described by way of example. Milk, skim milk, cream, natural cheese and processed cheese are irradiated with near infrared having a specific wavelength from 700 to 1200 nm and the quantity (or quantities) of such specific near infrared transmitted by these dairy products is determined. Simultaneously, a component (or components) is/are determined by the chemical analysis according to the official method.

Such procedures are repeated for a plurality of subjects, preferably for 50 or more samples.

Then, the optimal value of component conversion factor is determined by using a equation of multiple linear regression so that the contents of respective target compositions can be determined by the near infrared measurement on the basis of the value(s) obtained by the chemical analysis. Thereafter, said value of conversion factor is used to make a calibration curve to be utilized for the near infrared measurement.

A specific embodiment of such method will be described below as it is applied to a determination of a fat content in milk. A calibration curve for the fat content (C %) of milk is approximately expressed by $$C\% = K_1 + K_1\lambda_1 + K_2\lambda_2 \quad (1)$$

where $\lambda_1$, $\lambda_2$ represent absorptivities corresponding to specific wavelengths of 884 nm, 1134 nm, respectively, correlated with the fat content and depending on a particular sample as well as component. K represents a proportional constant also depending on a particular sample and component and corresponding to the value of a conversion factor for the component. Here is used the multiple linear regression, one of the multivariant analysis procedures, to determine a proper value of K so as to provide the maximum coefficient of correlation between the fat content determined by the chemical analysis and the value estimated by equation (1) and to provide the minimum difference between the estimated value and the chemically analyzed value.

The regression equation (1) containing $K_n$ and $\lambda_n$ is adequately fit for practical use with n=2, i.e., it suffices for the regression equation (1) to contain $K_1$, $\lambda_1$, $K_2$ and $\lambda_2$. It is known that setting a pair of specific wavelengths for every component results in an improvement of the analysis precision compared to the case in which a single wavelength is set for every component. For practical use, it suffices to set a pair of special wavelengths and setting three or more values of $K_n$ and $\lambda_n$ for every component never leads to a significant improvement of the precision with respect to the case in which a pair of special wavelengths are set for every component.

In general, use of three or more specific wavelengths increases the correlation coefficient and reduces the standard deviation so that the analysis precision is theoretically improved.

Accordingly, the larger the number of specific wavelengths, the higher the analysis precision will be. However, such improvement of the analysis precision is meaningful only for the samples having been used to make the calibration curve (so-called overfitting) and meaningless for analysis of unknown samples. To avoid such overfitting, a pair of wavelengths will suffice when the number of samples to be analyzed is in the order of fifty.

The reason for which, instead of a single wavelength, a pair of wavelengths are employed lies in that, generally when a target composition is determined utilizing NIR (Near Infrared), a wavelength having a high correlation with the target composition, e.g., a typical wavelength having a relatively dominant absorbancy is used as a first wavelength (i.e., primary term) and a wavelength having a low correlation with the target composition, e.g., a typical wavelength having an absorbancy corresponding to a relatively nondominant molecular combination in the composition as a second wavelength (i.e., secondary term). (There is also an exceptional case in which both the wavelengths used have high correlation with the target composition.)

For example, when the fat content is determined, an absorption band for the C—H combination which reflects a molecular structure of fat is used as the first wavelength and an absorption band for the O—H or N—H combination having no relation with the fat molecular structure is used as the second wavelength.

A calibration equation could be prepared by using only the first wavelength having a high correlation coefficient but this would often not provide a significant improvement of the analysis precision, because the quantity of transmitted radiation slightly fluctuates even for the same wavelength, depending upon actual state of the sample (factors such as thickness, temperature and pH of the sample, size and color of a fat globule). The second wavelength is necessary to compensate for the fluctuation in the quantity of transmitted radiation due to such noises.

In an exceptional case in which it is desired to determine a total solid content, sometimes a pair of wavelengths both having high correlation coefficients are used.

Specifically, there is no absorption band corresponding to the total solid in absorption bands of NIR. However, the total solid in milk can be considered to be equal to fat plus protein, so the absorption bands for fat and protein, respectively, can be used to prepare the calibration equation. Accordingly, both of the wavelengths used will have high correlation coefficients. In such case, a wavelength having a low correlation coefficient may be used as the third wavelength to compensate for said noises. However, it is undesirable to use such third wavelength in consideration of the previously mentioned overfitting which should be avoided.

Once the calibration curve has been prepared in the manner as described above, the sample is irradiated with the near infrared of the wavelengths having been used to prepare the calibration curve, thereby an absorbancy is determined and $\lambda_1$, $\lambda_2$ in the equation (1) is substituted by this absorbancy to determine the composition.

Fat contents of 75 milk samples determined in this manner utilizing NIR were compared to those determined from the chemical analysis (official method) of the same samples and thereby a correlation coefficient of 0.997 and a standard error of calibration of 0.076 were obtained. Analytic value obtained by the official method is designated by A, analytic value obtained by utilizing NIR according to the invention is designated by B, and these values A, B are shown together with a difference B−A in Table 1. The same is graphically shown by FIG. 1 in which the values obtained by the chemical analysis (official method) are shown as ordinates and the values obtained by NIR analysis are shown as abscissae. Table 1 and FIG. 1 indicate that the values obtained by NIR analysis have an adequate reliability.

TABLE 1

| Official chemical analytic values A | Inventive N I R analytic values B | Difference B-A |
|---|---|---|
| 3.530 | 3.414 | −.116 |
| 3.220 | 3.107 | −.113 |
| 3.380 | 3.298 | −.082 |
| 3.460 | 3.364 | −.096 |
| 3.310 | 3.194 | −.116 |
| 3.260 | 3.210 | −.050 |
| 3.200 | 3.114 | −.086 |
| 2.480 | 2.411 | −.069 |
| 3.210 | 3.147 | −.063 |
| 2.370 | 2.267 | −.103 |
| 2.640 | 2.578 | −.062 |
| 2.370 | 2.324 | −.046 |
| 2.010 | 1.913 | −.097 |
| 3.650 | 3.631 | −.019 |
| 3.250 | 3.241 | −.009 |
| 3.120 | 3.069 | −.051 |
| 3.450 | 3.392 | −.058 |
| 3.520 | 3.638 | .118 |
| 3.170 | 3.240 | .070 |
| 2.890 | 3.041 | .151 |
| 3.100 | 3.164 | .064 |
| 3.310 | 3.294 | −.016 |
| 2.840 | 2.871 | .031 |
| 2.920 | 2.919 | −.001 |
| 3.260 | 3.340 | .080 |
| 3.210 | 3.324 | .114 |
| 3.080 | 3.176 | .096 |
| 3.230 | 3.355 | .125 |
| 3.110 | 3.121 | .011 |
| 2.600 | 2.562 | −.038 |
| 3.580 | 3.558 | −.022 |
| 3.040 | 3.054 | .014 |
| 3.120 | 3.132 | .012 |
| 3.050 | 3.044 | −.006 |
| 3.070 | 3.110 | .040 |

TABLE 1-continued

| Official chemical analytic values A | Inventive N I R analytic values B | Difference B-A |
|---|---|---|
| 2.860 | 2.849 | −.011 |
| 2.530 | 2.476 | −.054 |
| 2.970 | 2.931 | .039 |
| 3.600 | 3.511 | −.089 |
| 3.260 | 3.204 | −.056 |
| 2.830 | 2.686 | −.144 |
| 3.630 | 3.507 | −.123 |
| 2.850 | 2.761 | −.089 |
| 3.560 | 3.443 | −.117 |
| 3.880 | 3.745 | −.135 |
| 3.690 | 3.603 | −.087 |
| 3.880 | 3.787 | −.093 |
| 3.730 | 3.671 | −.059 |
| 4.350 | 4.451 | .101 |
| 5.720 | 5.693 | −.027 |
| 6.390 | 6.346 | −.044 |
| 6.180 | 6.103 | −.077 |
| 5.490 | 5.472 | −.018 |
| 5.010 | 5.161 | .151 |
| 5.650 | 5.686 | .036 |
| 6.130 | 6.100 | −.030 |
| 5.770 | 5.674 | −.096 |
| 7.220 | 7.172 | −.048 |
| 5.390 | 5.513 | .123 |
| 6.000 | 5.883 | −.117 |
| 3.310 | 3.375 | .065 |
| 3.590 | 3.623 | .033 |
| 3.640 | 3.653 | .013 |
| 3.880 | 3.909 | .029 |
| 3.940 | 3.965 | .025 |
| 3.720 | 3.749 | .029 |
| 3.840 | 3.888 | .048 |
| 3.900 | 3.913 | .013 |
| 3.940 | 3.989 | .049 |
| 4.190 | 4.263 | .073 |
| 4.120 | 4.224 | .104 |
| 4.360 | 4.402 | .042 |
| 4.930 | 4.830 | −.100 |
| 3.730 | 3.775 | .045 |
| Correlation coefficient | 0.997 | |
| Standard error of calibration | 0.076 | |

Remainder components of milk to be measured such as total solid, protein, casein, lactose and salt can be measured in the identical manner.

By using the calibration curves prepared in the above-mentioned manner, the target compositions can be rapidly and nondestructively measured with a high precision without any special pretreatment.

The method of the invention further enables an ash content of skim milk as well as milk to be measured which has been unmeasurable by the conventional method.

The compositions in the ash content of milk that have relatively large absolute quantities include calcium and phosphate, and these inorganic components have conventionally been considered to be unmeasurable because they are inactive to IR and NIR. However, both calcium and phosphate are combined with protein in milk to form hydrophilic colloid and affect a N—H group which is a functional group in milk. Accordingly, the N—H bond absorptive wavelength of NIR may be utilized to determine the ash content in milk. There are several wavelengths which are N—H group absorptive and it was empirically found that the highest precision is achieved by using two specific wavelengths of said several wavelengths. Obviously it is also possible to use three or more wavelengths for the determination, as desired. In this way, the inventors successfully determined the ash content by the same method as the previously mentioned procedures used to determine the fat content.

As will be apparent from the foregoing, the invention selects a NIR region from 700 to 1200 nm and an optical path length from 1 to 15 mm which are suitable for transmittance measurement of various dairy products including liquid and solid products, then selects two or more specific wavelengths from said NIR range and, by using these specific wavelengths, rapidly and nondestructively determines respective contents of target components such as fat, total solid, protein, casein, lactose, salt and ash in each dairy product, with a high precision.

The wavelengths of near infrared with which the respective components contained in the various dairy products are irradiated and the optical path lengths for the respective dairy products will be set forth below:

| (A) Two or more specific wavelengths (unit: nm) | | |
| --- | --- | --- |
| | (a) | (b) |
| Fat | 840 to 940 | 1000 to 1150 |
| Total solid | 800 to 950 | 1040 to 1100 |
| Protein | 880 to 970 | 1050 to 1150 |
| Casein | 770 to 800 | 960 to 1000 |
| lactose | 750 to 780 | 1000 to 1070 |
| Salt | 800 to 920 | 1150 to 1200 |
| Ash | 700 to 770 | 950 to 1070 |

| (B) Specific optical path lengths (unit: mm) | |
| --- | --- |
| Milk and skim milk | 2 to 6, preferably 4 |
| Cream | 1 to 2, preferably 2 |
| Cheese | 2 to 15, preferably 10 |

It should be understood that the quantity of transmitted radiation decreases as the optical path length exceeds the range as set forth just above. In other words, it becomes difficult for the radiation to pass through the sample.

The present invention specifies the preferable optical path lengths for the respective dairy products, i.e., 2 mm for cream, 4 mm for skim milk and milk, and 10 mm for cheese. 1200 nm or higher wavelength of near infrared and infrared tends to be significantly absorbed by water and therefore has been considered to be unsuitable for analysis of the dairy product containing a large quantity of water. For effective analysis, it has usually been necessary to employ the reflective method of measurement or to adjust the optical path length to a value less than 0.5 mm. (Otherwise the radiation could not be transmitted by the sample.)

The wavelength range from 700 to 1200 nm utilized by the present invention is near to the visible region, so highly transmissive for water and can be used even to analyze the samples which are relatively high in water content.

Such high transmissivity for water allows said larger optical path length to be adopted and thereby to facilitate sample adjustment, because transmission of radiation is maintained. As a consequence, the measurement can be achieved with a high precision.

To measure components of milk, skim milk, and cream, a temperature of the sample is preferably adjusted to a range from 36° to 45° C., more preferably to a range from 39° to 41° C.

This is for the reason that, though it is unnecessary to set a strict temperature condition for a product such as cheese which is solid at the normal temperature, adjustment to a given temperature is essential for analysis of the liquid product such as milk. In the case of such liquid product, an excessively low temperature, e.g., 5° C. causes dew condensation on the sample cell. Reversely, an excessively high temperature, e.g., 50° C. leads to formation of film on a top surface of milk and causes a change in the compositions thereof. Accordingly, the temperature of the sample such as milk must be adjusted to the melting point (approximately 38° C.) of milk fat within said temperature range so that fat may be maintained in evenly dispersed condition.

Now an apparatus used to perform the actual measurement according to the method of the invention will be described in reference to FIG. 2 of the accompanying drawing.

In the Michelson interferometric optical system, well known to the art, light is emitted from a light source (1) and then having passed through a slit (2) is split by a beam splitter (3) into a pair of mutually orthogonal light components directed to a stationary mirror (4) and a movable mirror (5), respectively. After reflected on the mirrors (4), (5), these light components are combined together again by the beam splitter (3) and pass through a slit (6). It should be understood that there is provided drive means (14) to move the movable mirror (5) to a predetermined position.

The drive means (14) is connected to a computer (13) and controlled by a signal applied from this computer (13).

Figure 2:
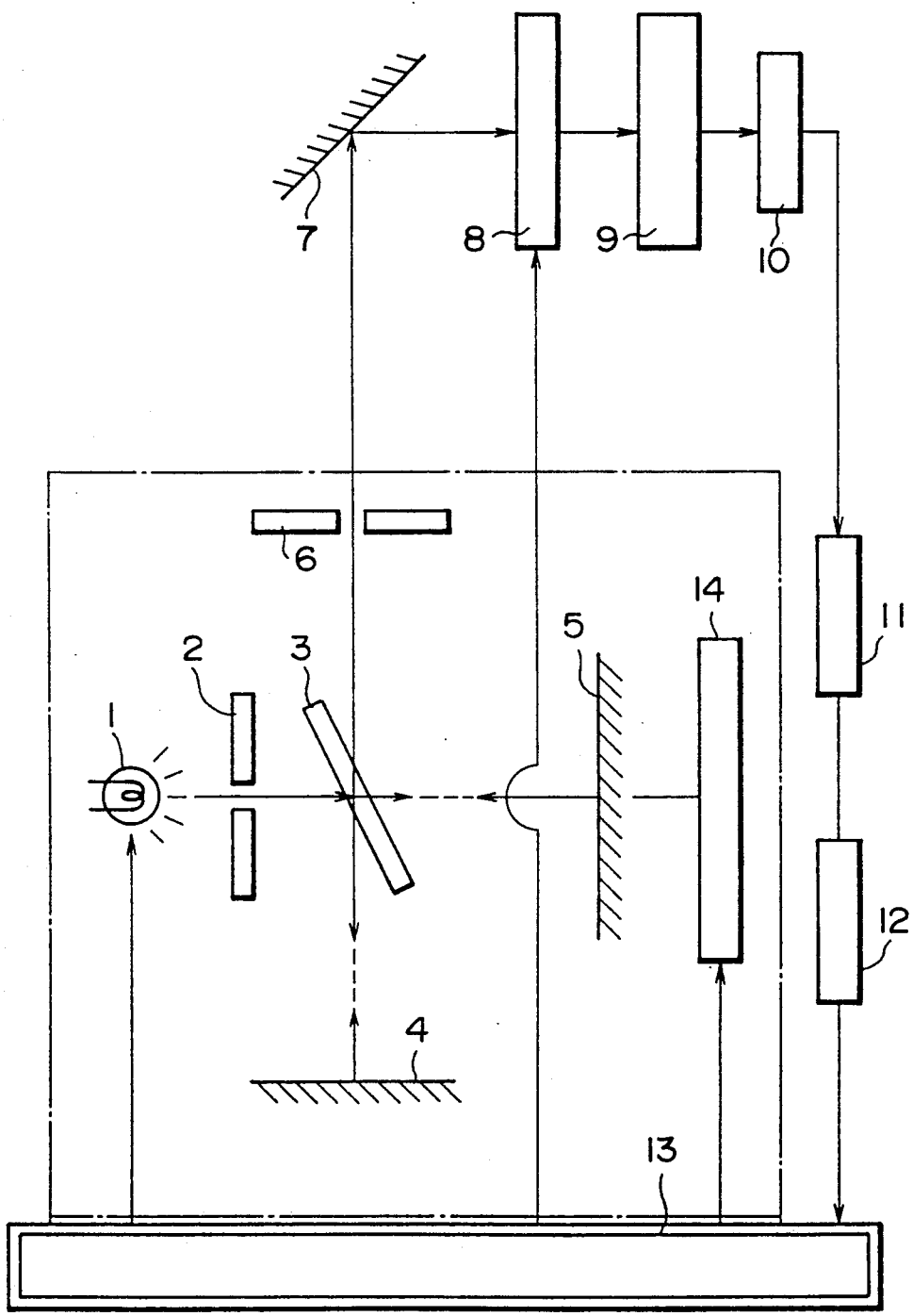
FIG. 2 is a schematic diagram showing the apparatus of the present invention.

Referring to FIG. 2, reference numeral (7) designates a reflective mirror adapted to reflect the light waves exiting through the slit (6) of the Michelson interferometric optical system toward a spectroscopic filter (8). An alternative arrangement may be adopted, in which said light waves having exited through the slit (6) are directly incident on the spectroscopic filter. In such arrangement, the reflective mirror (7) may be eliminated.

The spectroscopic filter (8) is interposed between the reflective mirror (7) and a sample cell (9), and the light waves of a specific wavelength band selected by passing through said filter are incident on the sample cell (9) through an entrance pupil.

The spectroscopic filters which can be used by the present invention are those having wavelength ranges of 700 to 800 nm, 820 to 950 nm, 960 to 1060 nm and 1070 to 1200 nm, respectively, and two or more filters having specific wavelengths in the respective ranges may be used.

It is preferred to employ a sample cell having an optical path length from 2 to 10 mm, but a sample cell having an optical path length from 1 to 15 mm is also acceptable. Within such acceptable range of optical path length, a specific optical length suitable for the particular type of dairy products may be selected.

The quantity of transmitted radiation is detected by a detector (10) adapted for photoelectric conversion of the quantity of transmitted radiation to a corresponding electric signal which is then amplified by an amplifier (11). The signal thus amplified is then converted by an A/D converter to a digital signal which is input to the computer (13).

Finally this apparatus shown by FIG. 2 employs the multiple regression equation to determine the respective components on the basis of said digital signal input to the computer (13).

The invention will be described in detail with reference to several experiments utilizing the method of the invention.

EXAMPLE 1

Employing the apparatus shown by FIG. 2 at a controlled temperature of 40 1, 74 samples of milk and 40 samples of skim milk both contained in crystal glass cuvette cells each having an optical path length of 4 mm were irradiated with pairs of NIRs having specific wavelengths, respectively, selected within the range from 700 to 1200 nm and quantities of these specific NIRs transmitted by the respective subjects were determined. It should be understood that the expression "a pair of specific NIRs corresponds to b in Table 2.

Simultaneously, wet chemical analysis (official method) was employed to determine contents of total solid, fat, protein, casein, lactose and ash in milk and contents of components except total solid and fat, i.e., protein, casein, lactose and ash in skim milk. Then, the multiple linear regression procedures were employed to determine the optimal conversion factor used for estimation of the target composition, said conversion factor being selected so as to provide the highest coefficient of correlation with the target composition as well as the minimum difference with respect to the value obtained by the chemical analysis, and a calibration equation was prepared on the basis of said conversion factor.

Respective pairs of specific wavelengths having been used to determine respective components of skim milk and milk are shown in Table 2 together with respective precisions of measurement (standard deviations).

TABLE 2

| Chemical compositions | Multiple correlation coefficient a | Specific wavelength (nm) b | Standard error |
|---|---|---|---|
| Total solid | 0.997 | 878; 1058 | 0.079 |
| Fat | 0.997 | 884; 1134 | 0.076 |
| Protein | 0.838 | 966; 1076 | 0.064 |
| Casein | 0.873 | 790; 966 | 0.054 |
| Lactose | 0.981 | 771; 1060 | 0.055 |
| Ash | 0.953 | 968; 1064 | 0.030 |

Values of a were determined from the regression equation.

b represents the respective pairs of selected wavelengths.

EXAMPLE 2

Employing the apparatus shown by FIG. 2 at a controlled temperature of 40 1, 70 samples of skim milk contained in crystal glass cuvette cells each having an optical path length of 4 mm were irradiated with pairs of NIRs having specific wavelengths, respectively, selected within the range from 700 to 1200 nm and quantities of these specific NIRs transmitted by the respective samples were determined. Expression "specific NIRs" corresponds to the specific wavelengths in Table 3.

At the same time, wet chemical analysis (official method) was employed to determine contents of total solid and fat, respectively, and a calibration equation was prepared by utilizing the multiple linear regression procedures just as in Example 1.

Respective pairs of specific wavelengths having been used to determine the respective contents of total solid and fat in skim milk are shown in Table 3 together with respective precisions of measurement (standard error).

TABLE 3

| Chemical compositions | Multiple correlation coefficient | Specific wavelength (nm) | Standard error |
|---|---|---|---|
| Total solid | 0.993 | 878; 1058 | 0.082 |
| Fat | 0.991 | 940; 1138 | 0.051 |

EXAMPLE 3

Employing the apparatus shown by FIG. 2 at a controlled temperature of 40 1, 30 samples of cream contained in crystal glass cuvettes each having an optical path length of 2 mm were irradiated with pairs of NIRs having specific wavelengths, respectively, selected within the range from 700 to 1200 nm and quantities of these specific NIRs transmitted by the respective samples were determined.

Simultaneously, wet chemical analysis (official method) was employed to determine contents of total solid and fat, respectively, and a calibration equation was prepared by utilizing the multiple linear regression procedures just as in Example 1.

Respective pairs of specific wavelengths having been used to determine the respective contents of total solid and fat in cream are shown in Table 4 together with respective precisions of measurement (standard error).

TABLE 4

| Chemical compositions | Multiple correlation coefficient | Specific wavelength (nm) | Standard error |
|---|---|---|---|
| Total solid | 0.995 | 928; 1060 | 0.119 |
| Fat | 0.999 | 931; 1140 | 0.188 |

EXAMPLE 4

Employing the apparatus shown by FIG. 2, 55 samples of natural cheese each dimensioned so as to have an optical path length (i.e., thickness of each sample) of 10 mm were irradiated with pairs of NIRs having specific wavelengths, respectively, selected within the range from 700 to 1200 nm and quantities of these specific NIRs transmitted by the respective subjects were determined.

At the same time, wet chemical analysis (official method) was employed to determine contents of total solid, fat, protein and salt, respectively, and a calibration equation was prepared by utilizing the multiple linear regression procedures just as in Example 1.

Respective pairs of specific wavelengths having been used to determine the respective components of natural cheese are shown in Table 5 together with respective precisions of measurement (standard error).

TABLE 5

| Chemical compositions | Multiple correlation coefficient | Specific wavelength (nm) | Standard error |
|---|---|---|---|
| Total solid | 0.991 | 907; 1047 | 0.432 |
| Fat | 0.973 | 845; 922 | 0.529 |
| Protein | 0.992 | 897; 1133 | 0.325 |
| Salt | 0.991 | 830; 1165 | 0.092 |

EXAMPLE 5

Employing the apparatus shown by FIG. 2, 70 samples of processed cheese each dimensioned so as to have an optical path length (i.e., thickness of sample) of 10 mm were irradiated with pairs of NIRs having specific wavelengths, respectively, selected within the range from 700 to 1200 nm and quantities of these specific NIRs transmitted by the respective subjects were determined.

Simultaneously, wet chemical analysis (official method) was employed to determine contents of total solid, fat, protein and salt, respectively, and a calibration equation was prepared by utilizing the multiple linear regression.

Respective pairs of specific wavelengths having been used to determine the respective components of processed cheese are shown in Table 6 together with respective precisions of measurement (standard error).

TABLE 6

| Chemical compositions | Multiple correlation coefficient | Specific wavelength (nm) | Standard error |
|---|---|---|---|
| Total solid | 0.997 | 825; 910 | 0.329 |
| Fat | 0.981 | 918; 1024 | 0.289 |
| Protein | 0.995 | 896; 1128 | 0.335 |
| Salt | 0.979 | 911; 1195 | 0.065 |

As will be apparent from the foregoing description, the method of the invention utilizes NIR to determine the respective components of dairy products and is not limited to the embodiments as have been set forth above as Examples 1 through 5.

The present invention allows the principal compositions of dairy products such as milk, natural cheese and processed cheese to be rapidly determined in nondestructive manner and, therefore is useful particularly for in-line quality control of dairy products.

What is claimed is:

1. Method for determining the principal constituents of dairy products comprising, providing a sample having a specific optical path length of from 1 to 15 mm, irradiating the sample with near infrared radiation of two or more specific wavelengths within the range of 700 to 1200 nm, measuring the quantities of the near infrared radiation transmitted by the sample and calculating the quantities of the constituents by using a multiple linear regression equation.

2. Method of claim 1, wherein a pair of specific wavelengths are used and a first wavelength thereof has a high correlation with a constituent and a second wavelength thereof has a low correlation with the constituent or both wavelengths have high correlations with the constituent.

3. Method of claim 2, wherein a fat content of the dairy products is determined and an absorption band for C—H bonds of the fat is used as the first wavelength and an absorption band for O—H and N—H bonds is used as the second wavelength.

4. Method of claim 1, wherein a total solid content of the dairy products is determined and two absorption bands highly correlated with fat and protein, respectively, are used.

5. Method of claim 1, wherein an ash content of the dairy products is determined and a pair of wavelengths both being absorbed by N—H groups are used.

6. Apparatus for determining the principal constituents of a dairy product, comprising:

(A) beam means for producing a beam of near infrared radiation;

(B) filter means disposed within said beam so as to produce a filtered beam having at least two specific radiation wavelength ranges within the overall range of 700 to 1200 nm;

(C) a sample means for containing a sample of the dairy product disposed within said filtered beam, said sample means having an optical path for said filtered beam of from 1 to 15 mm in length;

(D) a conversion means for receiving and converting the filtered beam transmitted through said sample means to electrical signals corresponding to absorbencies of the filtered beam by a sample of the dairy product disposed in the sample means;

(E) amplifier means for amplifying said electrical signals to amplified signals;

(F) digitizing means for converting the amplified signals to digital signals; and (G) digital processing means for processing the digital signals and calculating the quantities of constituents in the dairy product.

7. The apparatus of claim 6 wherein the specific radiation wavelength ranges are within the ranges of 700 to 800 nm, 820 to 950 nm, 960 to 1060 nm and 1070 to 1200 nm.

* * * * *